United States Patent

Jaeger

[11] Patent Number: 6,055,870
[45] Date of Patent: May 2, 2000

[54] SAMPLER FOR FLUIDIZED PRODUCT

[76] Inventor: Ben E. Jaeger, 50 Hunter La., Bristol, Ill. 60512

[21] Appl. No.: 09/338,667

[22] Filed: Jun. 22, 1999

[51] Int. Cl.[7] ........................................... G01N 1/04
[52] U.S. Cl. ............................................ 73/863.83
[58] Field of Search ........................... 73/863.51, 863.54, 73/863.52, 863.81–863.86, 864.34, 863.53, 863.55

[56] References Cited

U.S. PATENT DOCUMENTS

| | | |
|---|---|---|
| 4,147,062 | 4/1979 | Jaeger . |
| 4,262,533 | 4/1981 | Jaeger . |
| 4,475,410 | 10/1984 | Jaeger . |
| 4,630,479 | 12/1986 | Wagener et al. ..................... 73/863.83 |
| 4,744,255 | 5/1988 | Jaeger . |
| 5,585,576 | 12/1996 | Jaeger . |

*Primary Examiner*—Robert Raevis
*Attorney, Agent, or Firm*—Juettner Pyle & Piontek

[57] ABSTRACT

A sampling apparatus is characterized by a sampler body having a bore and a forward opening from the bore communicating with the interior of a vessel containing fluidized product in which strands, viscous strings and particles may be entrained. A plunger assembly in the bore is generally cylindrical along a longitudinal axis and has a sample receiver and cutters. The sample receiver is generally tubular and has a plurality of arcuately spaced longitudinal slots extending radially between an outer surface and a hollow interior of the sample receiver, and individual cutters are in facing relationship at opposite ends of the bore. A pneumatic motor reciprocates the plunger in the bore in a forward direction to a sample obtaining position where the sample receiver and cutters are extended at least partly out of the forward bore opening and into the interior of the process line to obtain a sample of fluidized product that flows into and fills the sample receiver passages and hollow interior. The motor then reciprocates the plunger rearward to a sample delivering position where said sample receiver and cutters are retracted into the bore for conveying the sample of fluidized product in the sample receiver to a sample delivery position in the bore. The sample receiver and cutters are a unitary structure and the cutters cooperate with the sampler body in both directions of reciprocation of the plunger assembly to slice through any strands, viscous strings and particles that extend radially outward from the sample receiver slots and would otherwise impede reciprocation of the plunger assembly.

28 Claims, 2 Drawing Sheets

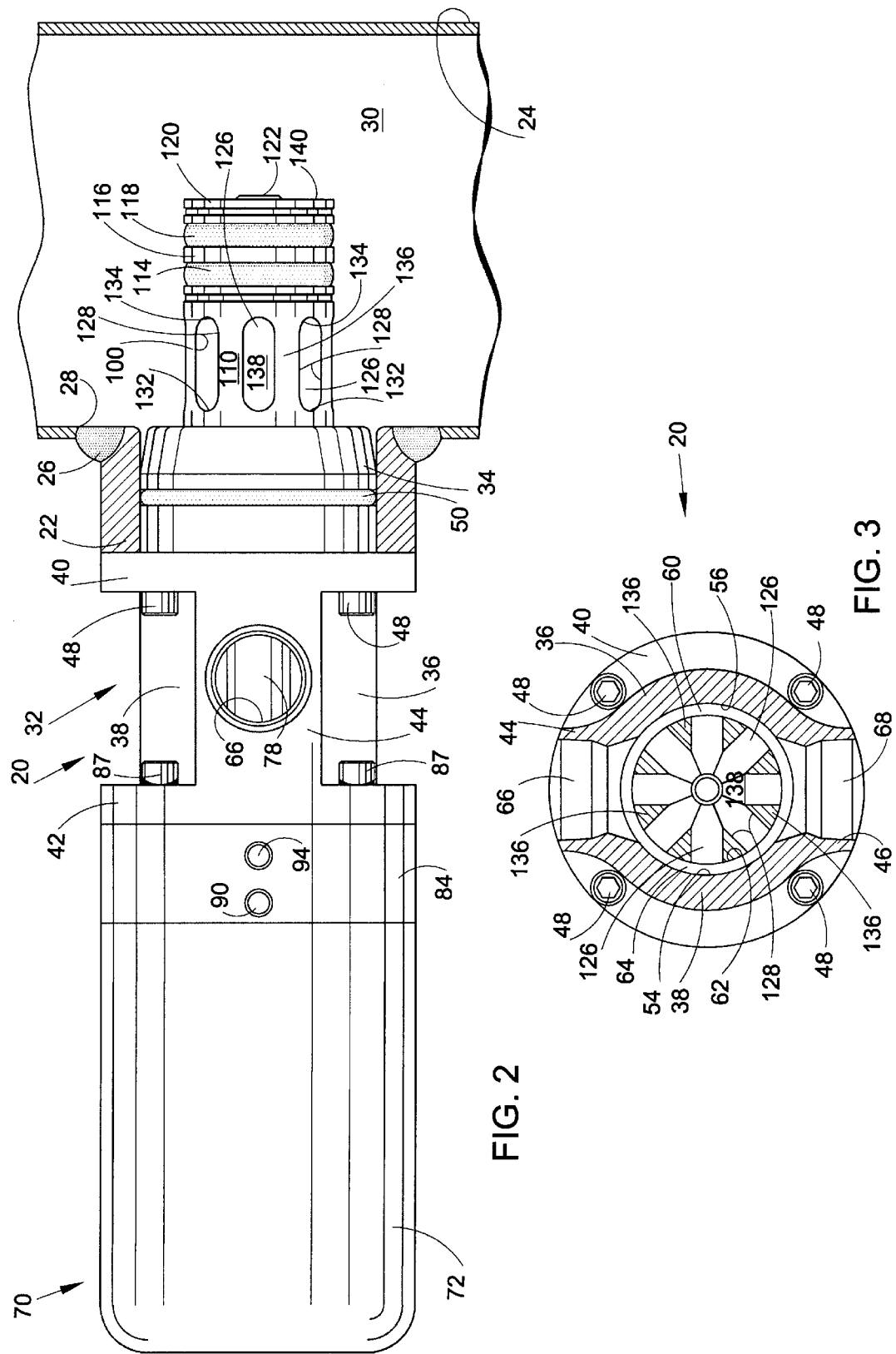

SAMPLER FOR FLUIDIZED PRODUCT

BACKGROUND OF THE INVENTION

The present invention relates to an apparatus for and a method of extracting samples of product from process lines, pipes or vessels. More particularly, the invention relates to an apparatus for and a method of extracting samples of a fluidized product, such as wood pulp slurry, in which strands, viscous strings and discrete particles may be entrained.

Certain manufacturing operations require that the immediate or overall composition of a liquid or fluid product flowing through a process line or contained within a vessel or tank be monitored. Such monitoring ordinarily is accomplished with sampling apparatus that takes samples of product from a main body of the product. Where a composite sample is required, the sampler may be periodically operated to withdraw a series of samples of a measured volume of product passing a sampling point. The individual samples are collected and admixed to form a composite representative of the total volume of product.

Other uses for samplers are in on-line analysis applications, in which the immediate composition of a product must be determined. For this application, the individual samples are analyzed separately.

With some other types of samplers, product flows into an opening in a probe and is then removed, for example by being conveyed through and out of the probe by the pressure of the product in the process line, by being gravitationally conveyed through and out of the probe, or by being collected within the probe for subsequent removal. Such samplers depend for proper operation on the ability of the product to flow into and/or out of the probe, and are not well suited for sampling product that has a tendency to plug up the probe opening or coagulate within the probe.

Another type of sampler continuously diverts a stream of product from a process line, and from the diverted stream samples are removed in various ways. Attempts to withdraw small, measured quantities directly from a line, however, have presented problems not altogether satisfactorily solved. For example, in the case of a sampler comprising a probe that has a receiving hole or slot extended directly into a pipe, the sampler often requires an orienting mechanism, and sampled product can build up in such holes and slots and either block the sampler or contaminate subsequent samples.

With some samplers, discrete samples are removed from a main body of product by extending a sample receiving chamber into, and then extracting the chamber from, product in the process line. Such samplers are usually characterized by a housing having a bore, with one end of the bore in communication with the interior of a product-containing vessel. A plunger is in the bore and has a sample receiving chamber in the form of a recess intermediate its ends. Means are provided for reciprocating the plunger in the bore to project the recess into the vessel to receive a sample of product therein, and to then retract the recess and product sample from the line to a sample collection point in the bore. Seals on the plunger to opposite sides of the recess maintain a seal between the product in the process line and the sample collection point during reciprocation of the plunger. Four exemplary types of such prior samplers are disclosed in U.S. Pat. Nos. 4,147,062, 4,262,533, 4,475,410 and 4,744,255, issued to Ben E. Jaeger, the present inventor and teachings of which patents are incorporated herein by reference. Sampling apparatus of the type disclosed in said patents is attached to a port to a process line or vessel containing the liquid or fluid product to be sampled. This enables a sample chamber in a plunger of the sampler to be extended into the product to receive a product sample in the chamber. The plunger is then retracted to deliver the product sample to the collection point in the sampler.

Conventional samplers of the above type operate satisfactorily with product that is relatively fluent and of generally uniform consistency, but they often are less than satisfactory for sampling fluidized product in which strands, viscous strings and relatively large discrete particles are entrained, such as wood pulp slurry containing knots. It is difficult for a conventional sampler to convey such product to a collection point within the sampler, since the particulate material in the product can block openings in the sampler and otherwise interfere with movement and proper operation of the sampler.

A prior sampler that is adapted to sample fluidized product containing relatively large particulate material is disclosed in U.S. Pat. No. 5,585,576, issued to Ben E. Jaeger, the present inventor and the teachings of which are incorporated herein by reference. The sampler of said patent has a housing with a bore that communicates at one end with the interior of a process line or vessel containing fluidized product. A plunger assembly in the bore has a sample chamber intermediate its ends and is reciprocated to project the sample chamber out of the bore and into the vessel to receive a sample of product therein, and to then retract the sample chamber from the vessel and into the bore to a sample collection point. A rearward facing cutter on the plunger, at a forward end of the sample chamber, cooperates with the housing at the one end of the bore, upon retraction of the plunger, to slice through any particulate matter that may be extending partially out of the sample chamber and that would otherwise interfere with retraction of the plunger into the bore. Forward and rearward plunger seals on opposite sides of the sample chamber always maintain a liquid seal between the one end of the bore and the sample collection point. The rearward seal comprises a shear bearing having a circumferential groove that receives and retains fluidized product in sealing relation to the bore to seal the shear bearing and thereby the plunger assembly to the bore. The product collection point in the bore includes a plurality of passages in the housing that communicate with the bore and are sized to prevent passage therethrough of relatively large product particles. Upon reciprocation of the plunger assembly to project the sample chamber into the vessel, the shear bearing cuts off and conveys back into the vessel any pieces of product that may have become caught in the passages during the previous sampling cycle and that extend into the bore.

While samplers constructed according to said U.S. Pat. No. 5,585,576 have been successfully used to sample fluidized fibrous product such as wood pulp, depending upon the nature of the product and its flow velocity, extending the forward end of the plunger into the product flow can sometimes result in destruction of the plunger. This can occur because the sample chamber of the plunger is annular in shape and defined around a relatively small diameter stem that connects the plunger forward end to the plunger rearward end. Because it has a relatively small diameter, the resistance of the stem to longitudinal bending is relatively limited. Should the product being sampled have a flow velocity that is unusually high and turbulent, when the plunger is extended into the product flow to obtain a sample, the force exerted by the product on the plunger forward end can bend the stem longitudinally and destroy the plunger. Even if the stem is not bent enough to destroy the plunger, limited bending can result in the rearward facing cutter at the front of the sample chamber being impacted against the housing at the front end of the housing bore upon retraction of the plunger, which can severely damage the cutter and housing.

OBJECTS OF THE INVENTION

An object of the present invention is to provide an improved sampler that is particularly adapted to sample a fluidized product in which particles of a relatively large size are entrained, for example a product such as wood pulp containing knots.

Another object is to provide such a sampler that includes a reciprocable plunger assembly defining a sample chamber that is extended into and out of the product to receive and deliver discrete samples of the product to a collection point.

A further object is to provide such a sampler in which a seal is always maintained between product being sampled and the collection point.

Yet another object is to provide such a sampler in which the plunger carries a cutter that cuts through strands, viscous strings and relatively large particles that would otherwise impede reciprocation of the plunger, in both forward and rearward directions of reciprocation of the plunger.

A still further object is to provide such a sampler in which the cutter is cylindrical and coaxial with the plunger, the sample chamber is defined within an interior of the cutter, and the cutter and sample chamber are a one-piece unit.

Still another object is to provide such a sampler in which the cylindrical cutter is of substantially the same overall diameter as the plunger and acts as a guide in supporting the plunger for reciprocation within a bore in a housing of the sampler.

SUMMARY OF THE INVENTION

In accordance with the present invention, a sampling apparatus comprises a fluid sampler for obtaining discrete samples of a fluidized product in which strands, viscous strings and/or relatively large particles are entrained. The fluid sampler includes a sampler body having a bore and a forward opening from the bore at a forward end of the body. A plunger means in said sampler body bore is generally cylindrical along a longitudinal axis and includes sample receiving means and cutting means. The sample receiving means is generally tubular and has a plurality of arcuately spaced passages extending radially between an outer surface and a hollow interior of the sample receiving means. Included are means for coupling the sampling apparatus to a process line containing fluidized product, with the sampler body bore forward opening in communication with an interior of the process line. Also included is motor means for reciprocating the plunger means in the bore in a forward direction to a sample obtaining position where the sample receiving means and cutting means are extended at least partly out of the forward bore opening and into the interior of the process line for obtaining a sample of fluidized product that flows into and fills the sample receiving means passages and hollow interior. The motor means also reciprocates the plunger means in a rearward direction to a sample delivering position where the sample receiving means and cutting means are retracted into the bore for conveying the sample of fluidized product in the sample receiving means to a sample delivery position in the bore. During reciprocation of the plunger means, the cutting means cooperates with the sampler body, in both directions of reciprocation of the plunger means, to slice through any strands, viscous strings or product particles that extend radially outward from the sample receiving means passages and would otherwise impede reciprocation of the plunger means. Advantageously, the sample receiving means and the cutting means comprise a unitary structure.

In the preferred embodiment, the sample receiving means passages are longitudinally extending slots that are equally arcuately spaced around the sample receiving means. The sampler receiving means is generally triangular in radial cross section between adjacent pairs of the slots, and the slots lie in a circle around a circumference of the sample receiving means. The sampler body bore has an annular chamber at the sample delivery position, the annular chamber has a diameter greater than that of the bore forward from the annular chamber, and when the plunger means is reciprocated to the sample delivering position, the annular chamber then extends around and along the slots for receiving product delivered from the sample receiving means through the slots.

It is contemplated that seal means be used to maintain a seal between the sampler body bore forward opening and the sample delivering position in the bore during reciprocation of the plunger means. The seal means comprises elastomeric material seals on the plunger means both rearward and forward from the sample receiving means and the cutting means, and the rearward seals move across, past and forward from the sample delivering position in the sampler body bore upon forward reciprocation of the plunger means. The sampler body has a product sample outlet port and an expelling fluid inlet port extending in diametric opposition between the annular chamber and an exterior of the sampler body, the sample outlet port conveys to an external collection point product samples received in the annular chamber from the sample receiving means, and the expelling fluid inlet port conveys to the annular chamber and the sample receiving means any expelling fluid that may be used to expel a product sample through the product sample outlet port.

The invention also contemplates a method of sampling a fluidized product in which strands, viscous strings and/or relatively large particles are entrained. The method comprises the step of providing a sampler body that has a longitudinal bore and a forward opening from the bore at a forward end of the body. Included is the step of positioning a longitudinally elongate plunger, having a sample obtaining sample receiver and particle cutters intermediate forward and rearward ends thereof, in the bore, wherein the sample receiver is generally tubular and has a plurality of arcuately spaced passages extending radially between an outer surface and a hollow interior thereof and the particle cutters are individual cutters at opposite longitudinal ends of the passages. Also included are the steps of coupling the sampler body to a process line containing fluidized product, with the sampler body bore forward opening in communication with an interior of the process line, and reciprocating the plunger in the bore in a forward direction to a sample obtaining position where the sample receiver and particle cutters are extended at least partly out of the forward bore opening and into the interior of the process line for obtaining a sample of fluidized product that flows into and fills the sample receiver passages and hollow interior, and then in a rearward direction to a sample delivering position where the sample receiver and cutters are retracted into the bore for conveying the sample of fluidized product in the sample receiver to a sample delivery position in the bore. Upon retraction of the plunger, the cutters at the longitudinally forward ends of the passages are caused to slice through any strands, viscous strings and product particles that extend radially outward from the sampler receiver passages and would otherwise impede retraction of the plunger, and upon extension of the plunger the cutters at the longitudinally rearward ends of the passages are caused to slice through any strands, viscous strings or product particles that extend radially outward from the sample receiver passages and would otherwise impede extension of the plunger.

The foregoing and other objects, advantages and features of the invention will become apparent upon a consideration of the following detailed description, when taken in conjunction with the accompanying drawings.

BRIEF DESCRIPTION OF THE DRAWINGS

FIG. 2 is a top plan view of the sampler, partly in cross-section, showing the sampler in its sample collecting position, and FIG. 3 is a view, partly in cross-section, taken substantially along the lines 3—3 of FIG. 1.

DETAILED DESCRIPTION

Figure 1:
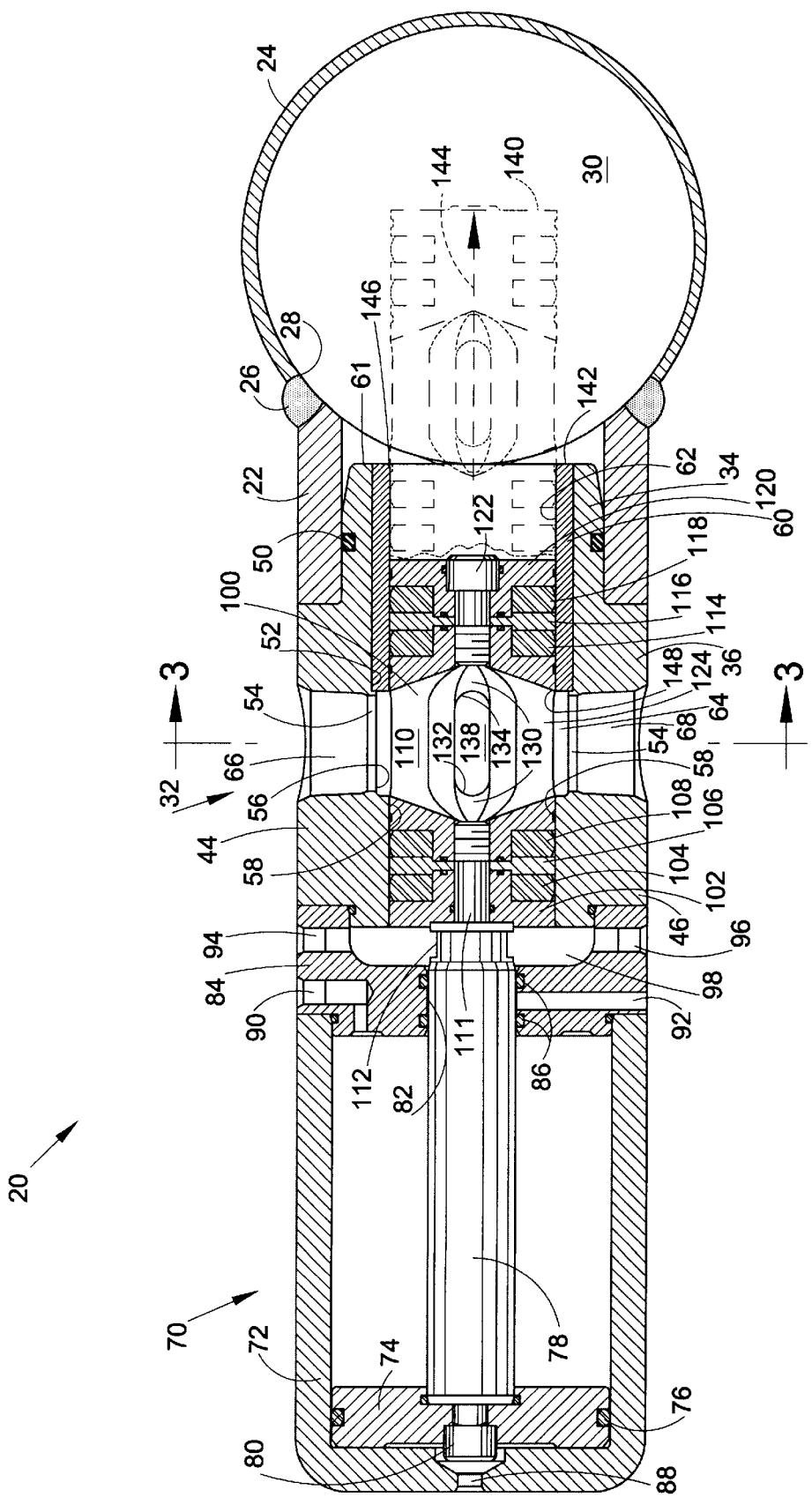
FIG. 1 is a cross-sectional side elevation view of a sampler embodying the teachings of the invention, showing the sampler in each of its sample collecting and sample delivering position.

There is shown in the drawings and indicated generally at 20 a sampler structured according to a preferred embodiment of the invention. The sampler is adapted for connection with an access line 22 to a process line, pipe or vessel 24, with the access line being connected by a weld 26 to the process line about an opening 28 to the line. Fluidized product is conveyed in a flow stream through an interior 30 of the process line. The sampler has a sampler body in which there is a bore and a plunger assembly is in the bore. The plunger assembly is reciprocable in the bore by a motor means between a first position where the plunger assembly is retracted rearward into the bore and a second position where the plunger assembly is extended forward at least partially out of the bore. In the second position, a sample collection chamber of the plunger assembly is extended into the process line to a product collection point for receiving a sample of the product. Upon rearward retraction of the plunger assembly to the first position, the sample chamber is moved to a sample delivery point in the bore where the sample is removed from the sample chamber. The sampler may be cyclically actuated so that the product samples are a composite of product flowing through the process line, and seals on the plunger assembly always maintain a liquid seal between the process line and interior and the sample delivery point within the sampler.

The sampler 20 is particularly adapted for obtaining samples of a fluidized product in which may be entrained strands, viscous strings and/or relatively large product particles, which in the following description will be collectively referred to as particles or product particles. So that the particles do not block movement of the plunger assembly and prevent proper operation of the sampler, the sampler includes a unique product particle cutter. The cutter is carried by and part of the plunger assembly. Upon reciprocation of the plunger assembly in either direction through the sampler body bore the cutter slices through any product particles that would otherwise interfere with movement of the plunger assembly. Advantageously, the cutter and sample chamber are a single structure that is configured to significantly increase the resistance of the plunger assembly to bending along its longitudinal axis.

More particularly, the sampler 20 comprises a body, indicated generally at 32. The body has an elongate cylindrical forward end 34 and a rearward end 36. The rearward end has a center semi-cylindrical portion 38, a flange 40 at the front of the center portion and a flange 42 at the back of the center portion. The rearward end 36 also has diametrically opposed ribs 44 and 46 extending radially outward from the center portion 38 between the flanges 40 and 42. To connect the sampler to the access line 22, the body forward end 34 is extended into the access line to abut the front flange 40 against the outer end of the access line. The sampler is then attached to the access line by a plurality of fasteners 48 extending between the flange 40 and the access line. An O-ring seal 50 carried by the body forward end provides a fluid tight connection between the forward end and the access line to prevent outward leakage of fluidized product from the process line 24.

Three coaxial passage sections extend through the sampler body 32. A first passage section 52 of a first diameter extends between a front end 61 of the body and an annular, radially inwardly extending shoulder 54. A second passage section 56 of a second diameter that is slightly less than the first diameter extends a short distance rearward from the rearward end of the first passage section. A third passage section 58 of a third diameter that is slightly less than the second diameter extends rearward from the second passage section to the rearward end of the body. A tubular sleeve 60 of a hardened wear resistant material is shrink-fit into the first passage section 52 and is of a length to extend between the shoulder 54 and a forward end of the first passage section. The inner diameter of the sleeve is the same as the third diameter of the third passage section 58. Therefore, since the second diameter of the second passage section is greater than the third diameter, the sleeve 60, second passage section 56 and third passage section 58 define a bore 62 through the body in which there is a medially located and enlarged diameter annular chamber 64 defined by and extending along the length of the second passage section. As will be described, the annular chamber is located at a sample delivering point in the bore to which collected product samples are delivered.

A fluid inlet port 66 extends through the rib 44 between the exterior of the sampler body 32 and the annular chamber 64 within the bore 62, and a product sample outlet port 68 extends through the rib 46 between the exterior of the body and the annular chamber. The ports are diametrically opposed on opposite sides of the bore.

Motor means for operating the sampler is indicated generally at 70. In the described embodiment the motor means is a pneumatic motor means, although other types of motor means could be used, such as electric or hydraulic motor means, depending upon the environment of the sampler. The motor means includes a cylinder 72 and a piston 74, carrying an annular seal 76 around its circumference, in the cylinder. A piston rod 78 is connected to the piston by a fastener 80 and extends forward from the piston through a passage 82 in a head 84. Within the passage a pair of seals 86 seals the piston rod to the head, and the head and seals serve to guide and support the piston rod during reciprocation. The head is connected to the forward end of the cylinder by any suitable means, such as by a plurality of fasteners (not shown) extending from the head rearward into the cylinder. The head also is connected to a rearward end of the body 32 by a plurality of fasteners 87 extending rearward through the sampler body flange 42 into the head. To reciprocate the piston, an air inlet 88 in the cylinder communicates with the cylinder interior on the rearward side of the piston and an air inlet 90 in the head communicates with the cylinder interior on the forward side of the piston. Pressurized air at the inlet 88 moves the piston and piston rod forward or rightward and pressurized air at the inlet 90 moves the piston and piston rod rearward or leftward. The head has a drain port 92 extending between the exterior of the head and the head passage 82 between the seals 86. The head also has a pair of diametrically opposed ports 94 and 96 extending between the exterior of the head and a space 98 between the head and the back end of the sampler body 32.

The sample collecting portion of the sampler 20 includes a plunger assembly, indicated generally at 100, connected to a forward end of the piston rod 78. The plunger assembly is reciprocable in the sampler body bore 62 by the motor means 70 between a first position where a sample chamber of the plunger assembly is retracted to the sample delivering point in the bore and a second position where the sample chamber is extended out of the bore to a sample collection point in the process line. The plunger assembly includes, on its left side as shown in FIG. 1 and from left to right, a carrier 102, an annular seal 104, an aligning plate 106, an annular seal 108 and a combination cutter/sample chamber, indicated generally at 110, of unitary structure. A threaded extension 111 at the front of the piston rod extends through the carrier 102, annular seals 104 and 108 and aligning plate 106 into threaded engagement with a rearward end of the cutter/sample chamber 110. The threaded extension holds the components together and under compression between the cutter/sample chamber and the piston rod and connects the plunger assembly to the piston rod. Wrench flats 112 on the piston rod accommodate tightly threading the piston rod extension into the cutter/sample chamber. The plunger assembly also includes, on its right side and from left to right, an annular seal 114, an aligning plate 116, an annular seal 118, a carrier 120 and a threaded fastener 122. The fastener extends rearward through the carrier 120, annular seals 114 and 118 and aligning plate 116 into threaded engagement with a forward end of the cutter/sample chamber 110 to hold the components together and under compression between the cutter/sample chamber and a head of the fastener. A plurality of O-ring seals (shown but not numbered) of the plunger assembly prevent leakage of product past the various components.

The cutter/sample chamber 110 is cylindrical and has cutting edges on its outer surface and a diameter slightly less than that of the inner diameter of the sleeve 60 and bore 62. The diameter of the cutter/sample chamber is such that it slides freely in the bore, yet cooperates with the circular edges of the sleeve at the front and rear of the bore, in both directions of reciprocation, to slice through any product particles that would impede reciprocation.

More particularly, the cutter/sample chamber 110 is made of hardened material and is tubular along a center portion 124 of its length. A plurality of elongate, longitudinally extending and equally arcuately spaced slotted openings extend radially between an outer surface and a hollow center of the center portion. Each slotted opening has sides 128 that that may be generally planar and parallel to each other and to the longitudinal axis of the center portion. Each slotted opening also has forward and rearward ends 130 that are cylindrical on their outer surface and recessed underneath with generally semicircular recesses that extend longitudinally outward and radially inward from the opening. The ends 130 of each slotted opening define, at the outer surface of the center portion, a curved knife-like rear cutting edge 132 and a curved knife-like front cutting edge 134. The front and rear cutting edges of each slotted opening are in facing relationship and each end 130 of a slotted opening increases in thickness in radial cross-section in the direction longitudinally outward from the opening. Forming the slotted openings 126 in the tubular center portion 124 defines, between adjacent pairs of openings, triangular and longitudinally extending ribs 136 that impart longitudinal bending resistance to the cutter/sample chamber. A hollow interior of the center portion and the interiors of the slotted openings in the center portion define a sample chamber 138 of predetermined volume.

In addition to the cutter/sample chamber, all of the other plunger assembly components, except for the seals 104, 108, 114 and 118, are of a slightly smaller diameter than the diameter of the bore 62. In consequence, the piston seal 76, the seals carried by the plunger assemble 100, along with the seals 86 in the head 84, control the concentricity of the plunger assembly and the piston rod 78 within the bore and head passage 82 and function as bearings to enable the plunger assembly and piston rod to reciprocate easily. This minimizes direct sliding contact between the relatively hard components of the sampler, whereby the life of the sampler is extended and its repair frequency reduced The sampler 20 is particularly adapted to obtain samples of fluidized product flowing through the interior 30 of the process line 24, in which product relatively large particulate matter is entrained. Such a product may comprise, for example, a fluidized wood pulp product in which is entrained strands, viscous strings a nd/or particles such as pieces of wood and knots. Prior samplers of conventional type, such as are disclosed in said aforementioned U.S. Pat. Nos. 4,147,062, 4,262,533, 4,475,410 and 4,744,255, are not fully satisfactory for use in obtaining samples of such products. With such samplers, product particles that enter a sampling chamber in a plunger of the sampler can block reciprocation of a p lunger in a bore in the sampler. In the present sampler 20, however, the forward cutting edge 132 and rearward cutting edge 134 cooperate with the sleeve 60 to slice through any material that might otherwise interfere with reciprocation of the plunger assembly 100. The cutting edges work to cut product particles in both directions of reciprocation of the plunger assembly, so that irrespective of whether the plunger assembly is being extended out of or retracted into the bore 62, such material does not block its movement. Product particles therefore do not interfere with operation of the sampler in obtaining samples of fluidized product.

The motor means 70 reciprocates the plunger assembly 100 to obtain samples of fluidized product from a product flow stream in the interior 30 of the process line 24. With the plunger assembly retracted to its first position as shown in solid lines in FIG. 1, a forward end 140 of the plunger assembly is withdrawn into the bore 62 to a position inward from both a forward end 61 of the sampler body 32 and a forward end 142 of the sleeve 60. In this position, the sampler is fully retracted out of a flow path through the process line so that scarifying plugs can be passed, if and as necessary, through the process line to remove any built up product from the process line inner wall. To obtain a sample of fluidized product, removing pressurized air from the inlet 90 and introducing pressurized air at the air inlet 88 energizes the motor means. This urges the piston 74 and piston rod 78 rightward or forward to move the plunger assembly forward from the first position to the second or sampling position, with the forward end 140 of the plunger assembly then being positioned as indicated by the head of an arrow 144 in FIG. 1 and as shown in FIG. 2. The length of the stroke of the motor means is determined by the distance between a front side of the piston and a rear side of the head 84, and is such that when the plunger assembly is in the second position, the slotted openings 126 are within the flow stream of product in the interior 30 of the process line 24. As the plunger assembly moves forward, the rearward plunger seals 104 and 108 move from behind the ports 66 and 68 to adjacent the front of the sampler body bore 62. In this manner, the seals 104 and 108 wipe the sampler body bore clean of any accumulated fluid product with each reciprocation of the plunger assembly. Also, as the plunger assembly is extended the rearward plunger seals 104 and 108 move past the ports 66 and 68 and form a fluid seal with the sampler body bore forward from the ports before the forward plunger seals 114 and 118 move out of the bore and into the process line. Similarly, upon leftward movement and retraction of the plunger assembly, the seals 114 and 118 enter the bore before the seals 104 and 108 move over the ports. In consequence, a fluid seal is at all times maintained between the fluid product in the process line and the inlet and outlet ports, and only the fluid sample obtained in the sample chamber ever reaches the sample delivery point in the bore at the ports.

With the plunger assembly 100 extended forward, the cutter/sample chamber is positioned within the interior 30 of the process line 24 and exposed to the flow stream of product. As a result, the sample chamber 138 is washed by the product flow, which cleans any old or contaminated product from the sample chamber. This occurs because the slotted openings 126 are spaced circumferentially around the cutter/sample chamber, so a portion of the flow of product enters the slotted openings facing upstream, flows though the inner chamber 138 and exits the slotted openings facing downstream. The sample chamber is therefore generally self-cleaning of debris that may be encountered in product lines, so that when it is withdrawn into the sampler bore 62, it will carry a valid sample of the fluidized product.

After extension of the plunger assembly 100 into the process line 24 to fill the sample chamber 138 with fluidized product, it is retracted into the sampler bore 62 to deliver a product sample in the sample chamber to the collection point between the ports 66 and 68. Because the product is a fluidized product and can be a slurry in which "debris" may be entrained, such as knots in the case of wood pulp product, the cutter edges 134 are provided at the forward ends of the slotted openings 126. These cutter edges, upon rearward retraction of the plunger assembly, cooperate with a circular edge 146 at the front of the bore 62 through the sleeve 60 to slice through any product particles, such as knots of wood, that may be extending radially outward of the slotted openings and that would otherwise prevent full retraction of the plunger assembly into the bore. This ensures complete retraction of the plunger assembly when the product being sampled contains particulate matter.

With the plunger assembly 100 fully retracted to bring the sample chamber 138 and product sample therein to the sample delivery point in the bore 62, the sample chamber is positioned, as shown in solid lines in FIG. 1, between the inlet and outlet ports 66 and 68. To facilitate removal of the product sample from the sample chamber, a stream of air or other suitable fluid or liquid can be applied through the fluid inlet port 66 to flush the sample from the chamber and through the outlet port 68. The enlarged diameter annular chamber 64 in the bore that surrounds the slotted openings 126 at the sample delivery point facilitates removal of the product sample from the sample chamber. Also, the annular chamber, together with the slotted openings being in a circular array, allows the plunger assembly to be free to rotate and eliminates any need for guides to prevent rotation of the plunger assembly. After exiting the sample chamber, the product sample flows through the outlet port 68 into any suitable collection device, such as into a container (not shown) connected to the port.

All product particles in the sample delivered to the collection point in the bore 62 may not necessarily exit the sample chamber 138. Instead, it can happen that one or more product particles remain partially in the sample chamber and partially extend radially outward from the slotted openings after the remainder of the sample is collected. Absent the unique design of the cutter/sample chamber 110, these particles would, upon forward extension of the plunger assembly 100, engage the rearward end of the sleeve 60 and impede extension of the plunger assembly. However, because of the forward cutting edges 132 at the rearward end of the slotted openings 126, upon the next forward extension of the plunger assembly, the cutting edges cooperate with a circular edge 148 at the rear of the bore 62 through the sleeve to slice though any radially outward extending particles so that they do not prevent full forward extension of the plunger assembly. The severed parts of the knots or other debris that remain behind in the enlarged annular chamber 64 ultimately pass through the outlet port 64 and those remaining in the sample chamber are carried forward and washed out of the sample chamber when it reenters the process line. The sampling cycle is then repeated.

The ports 94 and 96 provide specific advantages in monitoring the need for maintenance of the sampler. With the port 94 closed and the port 96 open, product dripping out of the port 96 visually indicates a need to replace the plunger seals 114 and 118 and/or 104 and 108. If desired, a sensor can be placed in the port 96 to sense any leakage of product and signal the need to replace the plunger seals. Use of a sensor is particularly advantageous if leakage of product from the sampler were highly undesirable and must be detected right away, such as where the product contains an insecticide or is radioactive. Alternatively, fluid may periodically be introduced at the port 94 to remove any product from the plunger and piston rod between the ports 94 and 96 and carry it to a sensor in the port 96 for detection.

The port 92 also serves the purpose of monitoring sampler seal integrity by providing a means to visually check the integrity of the seals 86 to opposite sides of the port. If the fluid used to operate the motor means 70 comes out of the port, that is an indication that the rearward seal 86 is worn. Should product exit the port, that indicates that the forward seal 86 requires replacement. Leakage of product out of the port 92 can also indicate that the port 96 is plugged and/or is not being properly monitored.

The invention therefore provides a novel sampler for fluidized product in which relatively large particles may be entrained. The sampler is not dependent for proper operation upon any particular rotational orientation of the plunger assembly 100. Instead, because the slotted openings 126 are uniformly arcuately spaced around the circumference of the cutter/sample chamber 110, irrespective of the rotational orientation of the plunger assembly, product samples will always be properly collected and delivered. The multiplicity of angled and curved cutting edges 132 and 134 at opposite ends of the slotted openings 126 act to slice through product particles protruding from the sample chamber during both extension and retraction of the plunger assembly. Also, the triangular ribs 136 spaced arcuately around and extending longitudinally along the circumference of the sample chamber add longitudinal strength and transverse rigidity to the cutter/sample chamber 110 and the plunger assembly 100.

Therefore, as compared to plunger assemblies of conventional samplers which often have a medially located annular sample chamber formed around a relatively small diameter axial stem, when used in sampling conditions where the product flow velocity is unusually high and turbulent, the plunger assembly 100 exhibits increased resistance to longitudinal bending and transverse deflection. Further, the cutter/sample chamber 110, by virtue of being cylindrical and of almost the same diameter as the bore 62, provides its own continuous guidance in the bore both when it exits and when it reenters the bore. The cutter edges 132 and 134 are therefore always in proper alignment to cooperate with the circular edges 146 and 148 of the sleeve 60 at opposite ends of the bore 62.

While one embodiment of the invention has been described in detail, various modifications and other embodiments thereof can be devised by one skilled in the art without departing from the spirit and scope of the invention, as defined in the accompanying claims.

What is claimed is:

1. Sampling apparatus, comprising:

a fluid sampler for obtaining discrete samples of a fluidized product in which particles may be entrained, said fluid sampler including a sampler body having a bore and a forward opening from said bore at a forward end of said sampler body;

plunger means in said sampler body bore, said plunger means being generally cylindrical along a longitudinal axis and including sample receiving means and cutting means, said sample receiving means being generally tubular and having a plurality of arcuately spaced passages extending radially between an outer surface and a hollow interior thereof;

means for coupling said sampling apparatus to a process line containing fluidized product, with said sampler body bore forward opening in communication with an interior of the process line, and motor means for reciprocating said plunger means in said bore in a forward direction to a sample obtaining position where said sample receiving means and cutting means are extended at least partly out of said forward bore opening and into the interior of the process line for obtaining a sample of fluidized product that flows into and fills said sample receiving means passages and hollow interior, and in a rearward direction to a sample delivering position where said sample receiving means and cutting means are retracted into said bore for conveying the sample of fluidized product in said sample receiving means to a sample delivery position in said bore, said cutting means cooperating with said sampler body in both directions of reciprocation of said plunger means to slice through any strands, viscous strings and product particles that extend radially outward from said sample receiving means passages and would otherwise impede reciprocation of said plunger means.

2. Sampling apparatus as in claim 1, wherein said sample receiving means passages are longitudinally extending slots.

3. Sampling apparatus as in claim 2, wherein said slots are equally arcuately spaced around said sample receiving means.

4. Sampling apparatus as in claim 3, wherein said sample receiving means is generally triangular in radial cross section between adjacent pairs of said slots.

5. Sampling apparatus as in claim 1, wherein said passages lie in a circle around a circumference of said sample receiving means, said sampler body bore has an annular chamber at said sample delivery position, said annular chamber has a diameter greater than that of said bore forward from said annular chamber, and said annular chamber extends around and along said passages, when said plunger means is reciprocated to said sample delivering position, for receiving product delivered from said sample receiving means through said passages.

6. Sampling apparatus as in claim 1, including seal means for maintaining a seal between said sampler body bore forward opening and said sample delivering position in said bore during reciprocation of said plunger means.

7. Sampling apparatus as in claim 6, wherein said seal means comprises elastomeric material seals on said plunger means both rearward and forward from said sample receiving means and said cutting means, said rearward seals moving past and forward from said sample delivering position in said sampler body bore upon forward reciprocation of said plunger means.

8. Sampling apparatus as in claim 5, including a product sample outlet port and an expelling fluid inlet port extending in diametric opposition between said annular chamber and an exterior of said sampler body, said sample outlet port conveying to an external collection point product samples received in said annular chamber from said sample receiving means and said expelling fluid inlet port conveying to said annular chamber and said sample receiving means any expelling fluid that may be used to expel a product sample through said product sample outlet port.

9. Sampling apparatus as in claim 1, wherein said cutting means comprises an individual cutting means at a forward end of each passage and at a rearward end of each passage.

10. Sampling apparatus as in claim 1, wherein said sample receiving means and said cutting means comprise a unitary structure.

11. Sampling apparatus as in claim 10, wherein said cutting means comprises an individual cutting means at a forward end of each passage and at a rearward end of each passage.

12. Sampling apparatus as in claim 11, wherein upon retraction of said plunger assembly from said sample obtaining position to said sample delivering position said cutting means at said forward ends of said passages cooperate with said sampler body at said forward opening from said bore to slice through any strands, viscous strings and product particles that extend radially outward from said sample receiving means passages, and upon extension of said plunger assembly from said sample delivering position to said sample obtaining position said cutting means at said rearward ends of said passages cooperate with said sampler body at said sample delivery position in said bore to slice through any strands, viscous strings and product particles that extend radially outward from said sample receiving means passages.

13. Sampling apparatus as in claim 12, wherein said sample receiving means passages are elongate longitudinal slots and said individual cutting means are in facing relationship at rearward and forward longitudinal ends of each said slot.

14. Sampling apparatus as in claim 13, wherein said cutting means have curved cutting edges.

15. Sampling apparatus, comprising:

a fluid sampler for obtaining discrete samples of a fluidized product in which strands, viscous strings and particles may be entrained, said fluid sampler including a sampler body having a bore and a forward opening from said bore at a forward end of said sampler body;

plunger means in said sampler body bore, said plunger means being generally cylindrical along a longitudinal axis and including sample receiving means and cutting means, said sample receiving means being generally tubular and having a plurality of arcuately spaced passages extending radially between an outer surface and a hollow interior thereof and said cutting means comprising an individual cutting means at opposite longitudinal ends of each passage;

means for coupling said sampling apparatus to a process line containing fluidized product, with said sampler body bore forward opening in communication with an interior of the process line, and motor means for reciprocating said plunger means in said bore in a forward direction to a sample obtaining position where said sample receiving means and cutting means are extended at least partly out of said forward bore opening and into the interior of the process line for obtaining a sample of fluidized product that flows into and fills said sample receiving means passages and hollow interior, and in a rearward direction to a sample delivering position where said sample receiving means and cutting means are retracted into said bore for conveying the sample of fluidized product in said sample receiving means to a sample delivery position in said bore, said cutting means cooperating with said sampler body in both directions of reciprocation of said plunger means to slice through any strands, viscous strings and product particles that extend radially outward from said sample receiving means passages and would otherwise impede reciprocation of said plunger means.

16. Sampling apparatus as in claim 15, wherein said sample receiving means and said cutting means comprise a unitary structure.

17. Sampling apparatus as in claim 15, wherein upon retraction of said plunger assembly from said sample obtaining position to said sample delivering position said cutting means at said forward ends of said passages cooperate with said sampler body at said forward opening from said bore to slice through any strands, viscous strings and product particles that extend radially outward from said sample receiving means passages, and upon extension of said plunger assembly from said sample delivering position to said sample obtaining position said cutting means at said rearward ends of said passages cooperate with said sampler body at said sample delivery position in said bore to slice through any strands, viscous strings and product particles that extend radially outward from said sample receiving means passages.

18. Sampling apparatus as in claim 17, wherein said sample receiving means passages are elongate longitudinal slots and said cutting means are in facing relationship at rearward and forward longitudinal ends of said slots.

19. Sampling apparatus as in claim 18, wherein said cutting means have a curved cutting edge.

20. Sampling apparatus as in claim 15, wherein said sample receiving means passages are longitudinally extending slots.

21. Sampling apparatus as in claim 20, wherein said slots are equally arcuately spaced around said sample receiving means.

22. Sampling apparatus as in claim 21, wherein said sample receiving means is generally triangular in radial cross section between adjacent pairs of said slots.

23. Sampling apparatus as in claim 15, wherein said passages lie in a circle around a circumference of said sample receiving means, said sampler body bore has an annular chamber at said sample delivery position, said annular chamber has a diameter greater than that of said bore forward from said annular chamber, and said annular chamber extends around and along said passages for receiving product delivered from said sample receiving means through said passages when said plunger means is reciprocated to said sample delivering position.

24. Sampling apparatus as in claim 15, including seal means for maintaining a seal between said sampler body bore forward opening and said sample delivering position in said bore during reciprocation of said plunger means.

25. Sampling apparatus as in claim 24, wherein said seal means comprises elastomeric material seals on said plunger means both rearward and forward from said sample receiving means and said cutting means, said rearward seal moving across, past and forward from said sample delivering position in said sampler body bore upon forward reciprocation of said plunger means.

26. Sampling apparatus as in claim 23, including a product sample outlet port and an expelling fluid inlet port extending in diametric opposition between said annular chamber and an exterior of said sampler body, said product sample outlet port conveying to an external collection point product samples received in said annular chamber from said sample receiving means and said expelling fluid inlet port conveying to said annular chamber and said sample receiving means any expelling fluid that may be used to expel a product sample through said product sample outlet port.

27. A method of sampling a fluidized product in which strands, viscous strings and particles may be entrained, comprising the steps of:

providing a sampler body having a longitudinal bore and a forward opening from the bore at a forward end of the sampler body;

positioning in the bore a longitudinally elongate plunger having a sample obtaining sample receiver and particle cutters intermediate forward and rearward ends thereof, wherein the sample receiver is generally tubular and has a plurality of arcuately spaced passages extending radially between an outer surface and a hollow interior thereof and the particle cutters are individual cutters at opposite longitudinal ends of the passages;

coupling the sampler body to a process line containing fluidized product, with the sampler body bore forward opening in communication with an interior of the process line;

reciprocating the plunger in the bore in a forward direction to a sample obtaining position where the sample receiver and particle cutters are extended at least partly out of the forward bore opening and into the interior of the process line for obtaining a sample of fluidized product that flows into and fills the sample receiver passages and hollow interior, and in a rearward direction to a sample delivering position where the sample receiver and cutters are retracted into the bore for conveying the sample of fluidized product in the sample receiver to a sample delivery position is the bore;

upon retraction of the plunger, causing the cutters at the longitudinally forward ends of the passages to slice through any strands, viscous strings and product particles that extend radially outward from the sampler receiver passages and would otherwise impede retraction of the plunger, and upon extension of the plunger, causing the cutters at the longitudinally rearward ends of the passages to slice through any strands, viscous strings and product particles that extend radially outward from the sample receiver passages and would otherwise impede extension of the plunger.

28. A method as in claim 27, including the step of maintaining a seal between the forward opening from the bore and the product delivery position in the bore during performance of said plunger reciprocation step.

* * * * *